United States Patent [19]
Robey et al.

[11] Patent Number: 5,750,332
[45] Date of Patent: May 12, 1998

[54] PEPTOMERS WITH ENHANCED IMMUNOGENICITY

[75] Inventors: Frank A. Robey, Bethesda; Tracy A. Harris-Kelson, Mitchellville; Marjorie Robert-Guroff, Rockville, all of Md.

[73] Assignee: The United States of America as represented by the Secretary of the Department of Health and Human Services, Washington, D.C.

[21] Appl. No.: 375,100

[22] Filed: Jan. 19, 1995

Related U.S. Application Data

[63] Continuation-in-part of Ser. No. 184,330, Jan. 19, 1994, abandoned.

[51] Int. Cl.⁶ .............................. C12Q 1/70; A61K 38/10
[52] U.S. Cl. .............................. 435/5; 514/2; 514/13; 435/974
[58] Field of Search .............................. 514/2, 841, 944, 514/13; 424/DIG. 14, 188.1, 196.11; 435/5, 974

[56] References Cited

U.S. PATENT DOCUMENTS

| | | | |
|---|---|---|---|
| 5,066,716 | 11/1991 | Robey et al. | 525/54.1 |
| 5,109,123 | 4/1992 | Reinherz et al. | 536/27 |
| 5,128,319 | 7/1992 | Arlinghaus | 514/12 |
| 5,185,147 | 2/1993 | Papsidero | 424/89 |

FOREIGN PATENT DOCUMENTS

| | | |
|---|---|---|
| WO 89/02277 | 3/1989 | WIPO. |
| WO 90/12868 | 1/1990 | WIPO. |
| WO 91/04273 | 4/1991 | WIPO. |

OTHER PUBLICATIONS

Robey, F.A., et al. (1994) "Use of peptomers to study the binding of HIV-1 to CD4: Effects of polymerication on the biology and chemistry of a synthetic peptide", *Peptides: Chemical, Structure and Biology*, Proc. Am Pept. Symp., 13th, Meeting date 1993;924–926.

Robey, F.A., et al. (1992) "Peptomers as Vaccine Candidates", *Genetically Engineered Vaccines*, 327:209–215.

Joklik et al., Zinsser Microbiology, 20th Edition. Appleton & Lange, Norwalk, conn., 1992, pp. 1053–1054.

Fahey et al., Status of Immune–based therapies in HIV infection and AIDS, Clin. exp. Immunol. 88:1–5, 1992.

*Primary Examiner*—Marian G. Knode
*Assistant Examiner*—Donna C. Wortman
*Attorney, Agent, or Firm*—Townsend and Townsend and Crew LLP

[57] ABSTRACT

The present invention relates to synthetic peptide analogues useful as therapeutic agents, immunogens or for the diagnosis of disease. In particular, it relates to peptide multimers which maintain the conformation of the native proteins from which they are derived. Peptomers constructed from peptides derived from gp120 of the human immunodeficiency virus are exemplified.

9 Claims, 9 Drawing Sheets

MRVKGIRRNYQHWWGWGTMLLGLLMICSATEKLWVTVYYGVPVWKEATTT 50

LFCASDAKAYDTEVHNWWATQACVPDTPNPQEVELVNVTENFNMWKNNMV 100

EQMHEDIISLWDQSLKPCVKLTPLCVTLNCDTLRNTTNTNNSTANNNSNS 150

EGTIKGGEMKNCSFNITTSIRDKMQKEYALLVKLDIVPIDNDSTSYRLIS 200

CNTSVITQACPKISFEPIPIHYCAPAGFAILKCNDKKFSGKGSCKNVSTV 250

QCTHGIRPVVSTQLLLNGSLAEEEVVIRSENFTDNAKTIIVHLNESVQIN 300

V3 LOOP

CTRPNYNKRKRIHIGPGRAFYTTKNIIGTIRQAHCNLSRSKWENTLKQIV 350

TKLRVQFKNKTIVFNRSSGGDPEIVMHSFNCGGEFFYCNTSPLFNSTWNG 400

CD4 BINDING REGION

NNTWNNTTGSNNNITLQC<u>KIKQIINMWQEVGKAMYA</u>PPIEGQIRCSSNIT 450

GLLLTRDGGKDTDTNDTEIFRPGGGDMRDNWRSELYKYKVVTIEPLGVAP 500

TKAKRRVVQREKRAAIGALFLGFLGAAGSTMGAASVTLTVQARLLLSGIV 550

QQQNNLLRAIEAQQHMLQLTVWGIKQLQARVLAVERYLKDQQLLGFWGCS 600

GKLICTTTVPWNASWSNKSLDDIWNNMTWMQWEREIDNYTSLIYSLLEKS 650

QTQQEKNEQELLELDKWASLWNWFDITNWLWYIKIFIMIVGGLVGLRIVF 700

AVLSIVNRVRQGYSPLSLQTRPPVPRGPDRPEGIEEEGGERDRDTSGRLV 750

HGFLAIIWVDLRSLFLFSYHHRDLLLIAARIVELLGRRGWEVLKYWWNLL 800

MHC II HOMOLOGY

QYWSQELKSSAVSLLNATAIAVA<u>EGTDRVI</u>EVLQRAGRAILHIPTRIRQG 850

LERALL 856

FIG. 1.

SEQUENCES FROM CD4 BINDING REGION OF GP120*

FROM HIV-1 SEQUENCES

| CONSENSUS 1 | RIKQIINMWQEVGKAMYA | (393-410) |
| HIVLAI | RIKQFINMWQEVGKAMYA | (433-441) |
| HIVHXB2R | RIKQIINMWQKVGKAMYA | (419-436) |
| HIVSC | RIKEIINMWQEVGKAMYA | (413-430) |
| HIVJRCSF | RIKQIINMWQEVGKAMYA | (411-428) |
| HIVMN | KIKQIINMWQEVGKAMYA | (419-436) |
| CONSENSUS 2 | RIKQIINMWQ?VGKAMYA | (369-386) |
| HIVELI | RIKQIIKMVAGRKAIYA | (416-433) |
| HIVU455 | RIKQIINMWQRVGQAMYA | (412-429) |

FROM HIV-2 SEQUENCES**

| HIV-2UC1 | HIKQIVNTWHKVGKYVYL | |
| HIV-2-CAM2 | HIRQIINTWHKVGKNVYL | |
| HIV-2-ISYR | HIEQIINTWHKVGKNVYL | (412-429) |

\* - FROM THE LOS ALAMOS HIV-1 DATA BASE

\*\* - BOLD LETTERS INDICATE HOMOLOGY WITH HIV-1

FIG. 2.

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 856 amino acids
        ( B ) TYPE: amino acid
        ( D ) TOPOLOGY: unknown ( i i ) MOLECULE TYPE: protein ( i i i ) HYPOTHETICAL: NO ( i x ) FEATURE:
        ( A ) NAME/KEY: Protein
        ( B ) LOCATION: 1..856
        ( D ) OTHER INFORMATION: /note= "Amino acid sequence of gp120 from HIV-1 isolate MN."

( i x ) FEATURE:
        ( A ) NAME/KEY: Region
        ( B ) LOCATION: 401..800
        ( D ) OTHER INFORMATION: /note= "CD4 binding region"

( x i ) SEQUENCE DESCRIPTION: SEQ ID NO:1:

```
Met Arg Val Lys Gly Ile Arg Arg Asn Tyr Gln His Trp Trp Gly Trp
 1               5                  10                  15

Gly Thr Met Leu Leu Gly Leu Leu Met Ile Cys Ser Ala Thr Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
    50                  55                  60

His Asn Trp Trp Ala Thr Gln Ala Cys Val Pro Asp Thr Pro Asn Pro
65                  70                  75                  80

Gln Glu Val Glu Leu Val Asn Val Thr Glu Asn Phe Asn Met Trp Lys
                85                  90                  95
```

| | | | | | | | | | | | | | | | |
|---|---|---|---|---|---|---|---|---|---|---|---|---|---|---|---|
| Asn | Asn | Met | Val<br>100 | Glu | Gln | Met | His<br>105 | Glu | Asp | Ile | Ile | Ser | Leu<br>110 | Trp | Asp |
| Gln | Ser | Leu | Lys<br>115 | Pro | Cys | Val | Lys<br>120 | Leu | Thr | Pro | Leu | Cys<br>125 | Val | Thr | Leu |
| Asn | Cys | Asp | Thr<br>130 | Leu | Arg | Asn | Thr<br>135 | Thr | Asn | Thr | Asn<br>140 | Asn | Ser | Thr | Ala |
| Asn<br>145 | Asn | Asn | Ser | Asn | Ser<br>150 | Glu | Gly | Thr | Ile | Lys<br>155 | Gly | Gly | Glu | Met | Lys<br>160 |
| Asn | Cys | Ser | Phe | Asn<br>165 | Ile | Thr | Thr | Ser | Ile<br>170 | Arg | Asp | Lys | Met | Gln<br>175 | Lys |
| Glu | Tyr | Ala | Leu<br>180 | Leu | Val | Lys | Leu | Asp<br>185 | Ile | Val | Pro | Ile | Asp<br>190 | Asn | Asp |
| Ser | Thr | Ser | Tyr | Arg<br>195 | Leu | Ile | Ser | Cys<br>200 | Asn | Thr | Ser | Val<br>205 | Ile | Thr | Gln |
| Ala | Cys<br>210 | Pro | Lys | Ile | Ser | Phe<br>215 | Glu | Pro | Ile | Pro | Ile<br>220 | His | Tyr | Cys | Ala |
| Pro<br>225 | Ala | Gly | Phe | Ala | Ile<br>230 | Leu | Lys | Cys | Asn | Asp<br>235 | Lys | Lys | Phe | Ser | Gly<br>240 |
| Lys | Gly | Ser | Cys | Lys<br>245 | Asn | Val | Ser | Thr | Val<br>250 | Gln | Cys | Thr | His | Gly<br>255 | Ile |
| Arg | Pro | Val | Val<br>260 | Ser | Thr | Gln | Leu | Leu<br>265 | Leu | Asn | Gly | Ser | Leu<br>270 | Ala | Glu |
| Glu | Glu | Val | Val<br>275 | Ile | Arg | Ser | Glu | Asn<br>280 | Phe | Thr | Asp | Asn | Ala<br>285 | Lys | Thr |
| Ile | Ile | Val<br>290 | His | Leu | Asn | Glu | Ser<br>295 | Val | Gln | Ile | Asn | Cys<br>300 | Thr | Arg | Pro |
| Asn<br>305 | Tyr | Asn | Lys | Arg | Lys<br>310 | Arg | Ile | His | Ile | Gly<br>315 | Pro | Gly | Arg | Ala | Phe<br>320 |
| Tyr | Thr | Thr | Lys | Asn<br>325 | Ile | Ile | Gly | Thr | Ile<br>330 | Arg | Gln | Ala | His | Cys<br>335 | Asn |
| Leu | Ser | Arg | Ser<br>340 | Lys | Trp | Glu | Asn | Thr<br>345 | Leu | Lys | Gln | Ile | Val<br>350 | Thr | Lys |
| Leu | Arg | Val<br>355 | Gln | Phe | Lys | Asn | Lys<br>360 | Thr | Ile | Val | Phe | Asn<br>365 | Arg | Ser | Ser |
| Gly | Gly | Asp<br>370 | Pro | Glu | Ile | Val | Met<br>375 | His | Ser | Phe | Asn | Cys<br>380 | Gly | Gly | Glu |
| Phe<br>385 | Phe | Tyr | Cys | Asn | Thr<br>390 | Ser | Pro | Leu | Phe | Asn<br>395 | Ser | Thr | Trp | Asn | Gly<br>400 |
| Asn | Asn | Thr | Trp | Asn<br>405 | Asn | Thr | Thr | Gly | Ser<br>410 | Asn | Asn | Asn | Ile | Thr<br>415 | Leu |
| Gln | Cys | Lys | Ile<br>420 | Lys | Gln | Ile | Ile | Asn<br>425 | Met | Trp | Gln | Glu | Val<br>430 | Gly | Lys |
| Ala | Met | Tyr<br>435 | Ala | Pro | Pro | Ile | Glu<br>440 | Gly | Gln | Ile | Arg | Cys<br>445 | Ser | Ser | Asn |
| Ile | Thr<br>450 | Gly | Leu | Leu | Leu | Thr<br>455 | Arg | Asp | Gly | Gly | Lys<br>460 | Asp | Thr | Asp | Thr |
| Asn<br>465 | Asp | Thr | Glu | Ile | Phe<br>470 | Arg | Pro | Gly | Gly | Gly<br>475 | Asp | Met | Arg | Asp | Asn<br>480 |
| Trp | Arg | Ser | Glu | Leu<br>485 | Tyr | Lys | Tyr | Lys | Val<br>490 | Val | Thr | Ile | Glu | Pro<br>495 | Leu |
| Gly | Val | Ala | Pro<br>500 | Thr | Lys | Ala | Lys | Arg<br>505 | Arg | Val | Val | Gln | Arg<br>510 | Glu | Lys |
| Arg | Ala | Ala | Ile<br>515 | Gly | Ala | Leu | Phe | Leu<br>520 | Gly | Phe | Leu | Gly | Ala<br>525 | Ala | Gly |

Ser Thr Met Gly Ala Ala Ser Val Thr Leu Thr Val Gln Ala Arg Leu
        530                 535                 540

Leu Leu Ser Gly Ile Val Gln Gln Asn Asn Leu Leu Arg Ala Ile
545                 550                 555                 560

Glu Ala Gln Gln His Met Leu Gln Leu Thr Val Trp Gly Ile Lys Gln
                565                 570                 575

Leu Gln Ala Arg Val Leu Ala Val Glu Arg Tyr Leu Lys Asp Gln Gln
            580                 585                 590

Leu Leu Gly Phe Trp Gly Cys Ser Gly Lys Leu Ile Cys Thr Thr Thr
        595                 600                 605

Val Pro Trp Asn Ala Ser Trp Ser Asn Lys Ser Leu Asp Asp Ile Trp
    610                 615                 620

Asn Asn Met Thr Trp Met Gln Trp Glu Arg Glu Ile Asp Asn Tyr Thr
625                 630                 635                 640

Ser Leu Ile Tyr Ser Leu Leu Glu Lys Ser Gln Thr Gln Gln Glu Lys
                645                 650                 655

Asn Glu Gln Glu Leu Leu Glu Leu Asp Lys Trp Ala Ser Leu Trp Asn
            660                 665                 670

Trp Phe Asp Ile Thr Asn Trp Leu Trp Tyr Ile Lys Ile Phe Ile Met
        675                 680                 685

Ile Val Gly Gly Leu Val Gly Leu Arg Ile Val Phe Ala Val Leu Ser
    690                 695                 700

Ile Val Asn Arg Val Arg Gln Gly Tyr Ser Pro Leu Ser Leu Gln Thr
705                 710                 715                 720

Arg Pro Pro Val Pro Arg Gly Pro Asp Arg Pro Glu Gly Ile Glu Glu
                725                 730                 735

Glu Gly Gly Glu Arg Asp Arg Asp Thr Ser Gly Arg Leu Val His Gly
            740                 745                 750

Phe Leu Ala Ile Ile Trp Val Asp Leu Arg Ser Leu Phe Leu Phe Ser
        755                 760                 765

Tyr His His Arg Asp Leu Leu Leu Ile Ala Ala Arg Ile Val Glu Leu
    770                 775                 780

Leu Gly Arg Arg Gly Trp Glu Val Leu Lys Tyr Trp Trp Asn Leu Leu
785                 790                 795                 800

Gln Tyr Trp Ser Gln Glu Leu Lys Ser Ser Ala Val Ser Leu Leu Asn
                805                 810                 815

Ala Thr Ala Ile Ala Val Ala Glu Gly Thr Asp Arg Val Ile Glu Val
            820                 825                 830

Leu Gln Arg Ala Gly Arg Ala Ile Leu His Ile Pro Thr Arg Ile Arg
        835                 840                 845

Gln Gly Leu Glu Arg Ala Leu Leu
    850                 855

( 2 ) INFORMATION FOR SEQ ID NO:2:

( i ) SEQUENCE CHARACTERISTICS:
      ( A ) LENGTH: 18 amino acids
      ( B ) TYPE: amino acid
      ( D ) TOPOLOGY: unknown ( i i ) MOLECULE TYPE: peptide ( i i i ) HYPOTHETICAL: NO ( x i ) SEQUENCE DESCRIPTION: SEQ ID NO:2:

Arg Ile Lys Gln Ile Ile Asn Met Trp Gln Glu Val Gly Lys Ala Met
1               5                   10                  15

Tyr Ala ( 2 ) INFORMATION FOR SEQ ID NO:3:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:3:

Arg Ile Lys Gln Phe Ile Asn Met Trp Gln Glu Val Gly Lys Ala Met
1               5                   10                  15

Tyr Ala ( 2 ) INFORMATION FOR SEQ ID NO:4:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:4:

Arg Ile Lys Gln Ile Ile Asn Met Trp Gln Lys Val Gly Lys Ala Met
1               5                   10                  15

Tyr Ala ( 2 ) INFORMATION FOR SEQ ID NO:5:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:5:

Arg Ile Lys Glu Ile Ile Asn Met Trp Gln Glu Val Gly Lys Ala Met
1               5                   10                  15

Tyr Ala ( 2 ) INFORMATION FOR SEQ ID NO:6:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:6:

Arg Ile Lys Gln Ile Ile Asn Met Trp Gln Glu Val Gly Lys Ala Met
1               5                   10                  15

Tyr Ala ( 2 ) INFORMATION FOR SEQ ID NO:7:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:7:

```
Lys Ile Lys Gln Ile Ile Asn Met Trp Gln Glu Val Gly Lys Ala Met
 1               5                  10                  15

Tyr Ala
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:8:

```
Arg Ile Lys Gln Ile Ile Asn Met Trp Gln Xaa Val Gly Lys Ala Met
 1               5                  10                  15

Tyr Ala
```

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:9:

```
Arg Ile Lys Gln Ile Ile Lys Met Val Ala Gly Arg Lys Ala Ile Tyr
 1               5                  10                  15

Ala
```

( 2 ) INFORMATION FOR SEQ ID NO:10:

( i ) SEQUENCE CHARACTERISTICS:
        ( A ) LENGTH: 18 amino acids
        ( B ) TYPE: amino acid
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:10:

```
Arg Ile Lys Gln Ile Ile Asn Met Trp Gln Arg Val Gly Gln Ala Met
 1               5                  10                  15

Tyr Ala
```

( 2 ) INFORMATION FOR SEQ ID NO:11:

( i ) SEQUENCE CHARACTERISTICS:
        ( A ) LENGTH: 18 amino acids (B) TYPE: amino acid
(D) TOPOLOGY: unknown (ii) MOLECULE TYPE: peptide (iii) HYPOTHETICAL: NO (xi) SEQUENCE DESCRIPTION: SEQ ID NO:11:

His Ile Lys Gln Ile Val Asn Thr Trp His Lys Val Gly Lys Tyr Val
1               5                   10                  15

Tyr Leu (2) INFORMATION FOR SEQ ID NO:12:

(i) SEQUENCE CHARACTERISTICS:
(A) LENGTH: 18 amino acids
(B) TYPE: amino acid
(D) TOPOLOGY: unknown (ii) MOLECULE TYPE: peptide (iii) HYPOTHETICAL: NO (xi) SEQUENCE DESCRIPTION: SEQ ID NO:12:

His Ile Arg Gln Ile Ile Asn Thr Trp His Lys Val Gly Lys Asn Val
1               5                   10                  15

Tyr Leu (2) INFORMATION FOR SEQ ID NO:13:

(i) SEQUENCE CHARACTERISTICS:
(A) LENGTH: 18 amino acids
(B) TYPE: amino acid
(D) TOPOLOGY: unknown (ii) MOLECULE TYPE: peptide (iii) HYPOTHETICAL: NO (xi) SEQUENCE DESCRIPTION: SEQ ID NO:13:

His Ile Glu Gln Ile Ile Asn Thr Trp His Lys Val Gly Lys Asn Val
1               5                   10                  15

Tyr Leu

PEPTOMERS WITH ENHANCED IMMUNOGENICITY

The present application is a continuation in part of application U.S. Ser. No. 08/184,330, filed Jan. 19, 1994 abandoned. The entire application is incorporated herein by reference.

BACKGROUND OF THE INVENTION

The present invention relates to synthetic peptide analogues useful as therapeutic agents, immunogens or for the diagnosis of disease. In particular, it relates to peptide multimers which maintain the conformation of the native proteins from which they are derived.

There is a growing interest in the construction of conformationally constrained synthetic peptides analogues for use in a number of applications such as rational design of novel drugs, development of immunogens, and as components of diagnostic immunoassays. One approach useful in this effort is the construction of peptide multimers or peptomers. Construction of such multimers have been described in the prior art (see, e.g., U.S. Pat. No. 5,066,716, U.S. Pat. No. 5,128,319, Hillman et al (1991), *Cell. Immunol.* 134: 1–13, and Borras-Cuesta et al. (1988), *Eur. J. Immunol* 18: 199–202). In certain circumstances, these peptide multimers have shown enhanced immunogenicity over the peptides from which they are derived.

This technology is particularly useful in the development of assays useful for the diagnosis of infections by human immunodeficiency virus (HIV), the causative agent for AIDS. For instance, in diagnostic immunoassays, a synthetic antigen must be recognized by antibodies cross-reactive with the native antigen on the viral surface. Thus, synthetic analogues of sequences from the envelope proteins of HIV must maintain the conformation of epitopes of the native protein. U.S. Pat. No. 5,128,319 describes the production of peptide multimers from sequences derived from gp120. Evidence provided in the patent, however, indicates that antibodies raised against the multimers described there are not cross reactive with HIV envelope proteins. U.S. Pat. Nos. 5,030,449, 5,081,226 and 5,283,323 disclose synthetic peptides derived from gp120.

Synthetic peptide analogues are also useful in the development of therapeutics and vaccines for the treatment and prevention of diseases such as AIDS. In the case of vaccines, safety concerns prevent the use of whole killed or attenuated HIV. Thus, most vaccines currently in clinical trials are subunit vaccines based on isolated envelope proteins from the virus. The disadvantage of this approach is that isolated proteins or fragments may be poorly immunogenic and may not contain correct epitopes to produce a protective immune response. To date, most reports of vaccines in clinical trials have been disappointing (Cohen (1993) *Science* 262: 980–981).

Thus, the development of synthetic analogues of sequences from proteins such as HIV envelope proteins which maintain conformational epitopes would be extremely useful in the development of diagnostic immunoassays and therapeutics. The present invention addresses these and other needs.

SUMMARY OF THE INVENTION

The present invention provides methods of detecting the presence of an antibody reactive with an HIV envelope protein in biological samples, such as blood samples. The methods comprise contacting the sample with a peptomer comprising a plurality of peptide monomers, each comprising a sequence from a CD4 binding region of gp120 from HIV, usually HIV-1. The formation of peptomer-antibody complexes is then detected.

The peptomer may be constructed using a number of techniques but are preferably constructed from haloacetyl-derivatized peptide monomers. The peptomers typically consist of about 2 to about 100 peptide monomers of about 6 to about 30 residues. A preferred peptide monomer is KIKQIINMWQEVGKAMYA (SEQ. ID. No. 7).

The diagnostic assays of the invention are usually carried out using the peptomer bound to a solid surface, such as the well of a microtiter plate. The peptomer-antibody complex is typically detected using a label, such as a detectable enzyme.

The invention further provides compositions comprising a peptomer of the invention, preferably those constructed from the peptide monomer KIKQIINMWQEVGKAMYA (SEQ. ID. No. 7) using haloacetyl chemistry. The peptomers of the invention can be used to block the binding of gp120 from HIV to CD4. Thus, the compositions can be used to inhibit infection of T cells by HIV.

Also provided are immunogenic compositions and methods for using them. The immunogenic compositions comprise an immunogenically effective amount of a peptomer of the invention along with a pharmaceutically acceptable carrier which preserves the secondary structure of the peptomer. The immunogenic compositions may further comprise an adjuvant, such as Ribi's adjuvant. Antibodies isolated from animals immunized according to the methods of the invention are also provided.

Finally, vaccine compositions comprising an immunogenically effective amount of a peptomer of the invention are provided.

Definitions

The term "peptomer" as used herein refers to a polymer of peptide monomers. A peptomer can be a homopolymer in which all of the peptide monomers have the same sequence or a heteropolymer in which the peptide monomers have different sequences. The peptomers are preferably conformationally constrained so that particular epitopes on peptide monomers of the peptomer are in a conformation that approximates the conformation in the native protein from which the peptide is derived. A number of methods may be used to construct peptomers of the invention. Peptomers of the invention are preferably made using the haloacetyl chemistry described below.

The term "peptide monomer" refers to a peptide unit used to construct a peptomer of the invention. The amino acid sequence of a peptide monomer can be derived from any biologically relevant protein, such as cellular receptors (e.g., interleukin receptors and the like) protein ligands recognized by those receptors, or a protein antigen against which an immune response is desired. Typically, the peptide monomers are modified to facilitate construction of the peptomers of the invention. Preferred modifications of the peptides include addition of a haloacetyl moiety at the N-terminus and a cysteine residue at the C-terminus. Particular methods for the production of peptomers from peptide monomers are described in more detail below.

A "pharmaceutically acceptable carrier which preserves the secondary structure of the peptomer" is a composition which preserves the secondary structure of the peptomer (i.e., either α-helix or βsheet) such that the secondary structure of the peptide monomers closely approximates the secondary structure of the native protein from which it is made. Typically, this will mean that the degree of α-helicity (if α-helical secondary structure is desired) of the peptomer in the pharmaceutical composition is at least about 20%, usually greater than about 30%, and in certain embodiments greater than about 50% as measured using circular dichroism spectroscopy as described in Provencher et al., (1981) Biochem. 20: 33–37. To preserve the secondary structure of the peptomers, the pharmaceutically acceptable carriers of the invention (including adjuvants) are preferably substantially aqueous solutions and do not comprise high concentrations of oils or other lipophilic compounds. Whether a particular carrier is suitable can easily be determined using the methods of Provencher et al. to measure the degree of α-helicity in the solution. Alternatively, antibodies raised against the compositions can be assayed for their ability to recognize the native protein.

The term "peptide" is used interchangeably with "oligopeptide" or "polypeptide" in the present specification to designate a series of residues, typically L-amino acids, connected one to the other typically by peptide bonds between the α-amino and carbonyl groups of adjacent amino acids.

The term "residue" refers to an amino acid or amino acid mimetic incorporated in an oligopeptide by an amide bond or amide bond mimetic.

BRIEF DESCRIPTION OF THE DRAWINGS

FIG. 1 shows the amino acid sequence of gp120 from the HIV-1 isolate MN (SEQ ID NO: 1).

FIG. 2 is a comparison of sequences from the CD4 binding regions of a number of HIV isolates SEQ ID NO: 2-13).

DESCRIPTION OF THE PREFERRED EMBODIMENT

The present invention provides synthetic analogues of desired proteins that can be used for the treatment and diagnosis of disease. The approach described below is particularly useful for the production of analogues in which conformational epitopes must be maintained. The following description focuses on peptomers of HIV envelope proteins used to detect antibodies to HIV, or as a therapeutic to interfere with the interaction of the virus and its target, human T cells. One of skill will recognize, however, that the methods described below can be used for other biologically relevant proteins, as well.

Many theories relate HIV to the development of AIDS. One hypothesis holds that AIDS is an autoimmune disease that is induced by chronic exposure of an individual to the envelope glycoprotein of HIV, gp160 and its major fragments gp120 and gp41. Research has shown that a region of gp160 shares amino acid sequence homology to a major protein of the immune system, MHC Class II β-chain (Golding et al. (1988) J.Exp.Med. 67: 914–923). Further work has shown sequence homologies between HIV-1 and other major components of the immune system such as antigen receptor molecules, immunoglobulins and T cell receptors (Sasal, et al. (1993) Vox Sang. 65:10–17). Because of these regions of shared sequence, an immune response against HIV-1 could result in an immune response against the immune system itself.

Researchers have also found that cross-linking CD4 via gp120-IgG complexes and, at the same time, cross-linking T cell receptors, leads to apoptosis, or programmed cell death (Terai et al. (1991) J. Clin. Invest. 87: 1710–1715). Apoptosis may account for the decrease in CD4-expressing cells that is observed in individuals suffering from AIDS. Thus, antibodies raised against certain regions of the gp120 may promote, rather than inhibit the development of disease.

Because of the potential of deleterious autoimmune responses, antibodies raised against gp120should be directed against regions of the protein that do not share homology with immune system proteins. For instance, the region of gp120 involved in binding of HIV to its cellular receptor, CD4, should avoid these problems. The region of gp120 apparently responsible for its high affinity binding to CD4 has been identified (Lasky et al. (1987) Cell 50: 975–985). Workers have also shown some minor binding of radiolabeled pentadecapeptides derived from this region to HeLa cells expressing CD4 (Reed et al. (1991) Biochem. 30: 4521–4527).

The amino acid sequence of gp120 from the MN isolate of HIV type 1 (HIV-1) is presented in FIG. 1 and SEQ ID NO. 1. There, the CD4 binding region, the V3 loop region and the MHC homologous region are shown. Although much of the sequence of this protein is hypervariable, the CD4 binding region is relatively well conserved.

Figure 3:
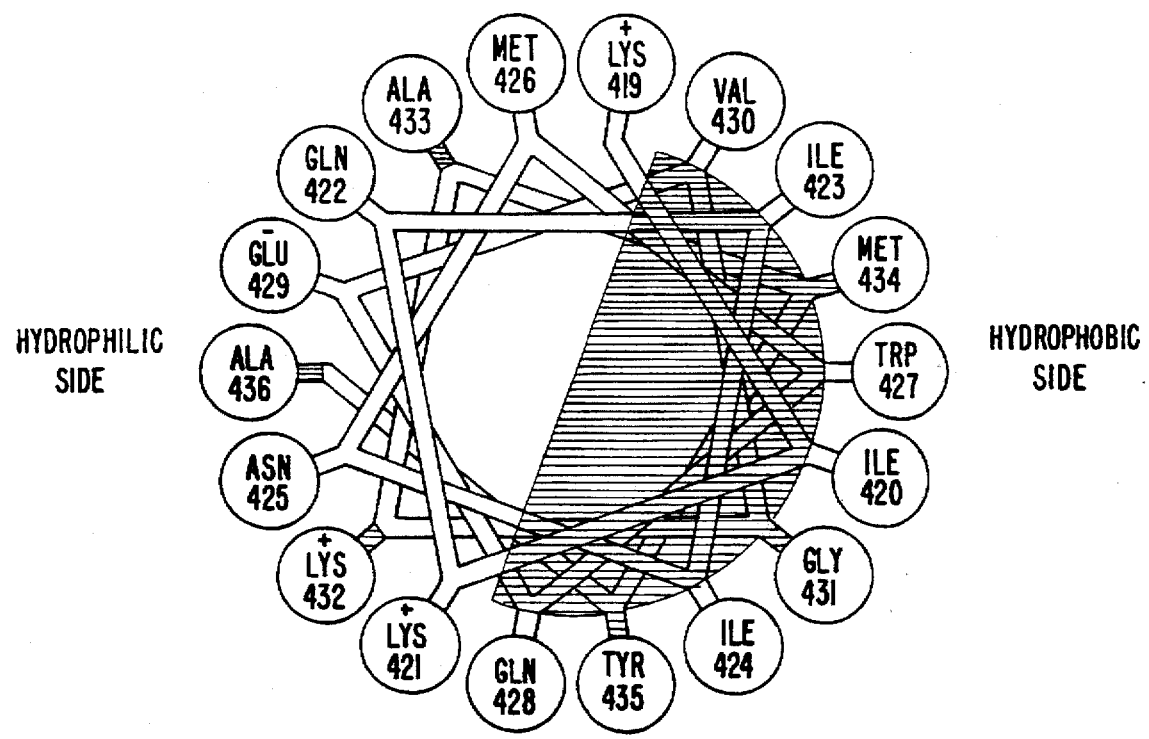
FIG. 3 shows residues 419-436 of gp120 from the MN isolate when placed in a conformational template referred to as a helical wheel.

A second HIV type (HIV-2) has also been described. It is believed to be more closely related to certain simian immunodeficiency viruses than to HIV-1. The envelope proteins of HIV-1 and HIV-2 share about 40% amino acid identity. The CD4 binding region of gp120 from HIV-2 has been mapped. Otteken et al. (1993) Virology 194:37–43. A comparison of sequences from the CD4 binding region of isolates of HIV-1 and HIV-2 is shown in FIG. 2 (SEQ ID NOS. 2-13). Close examination of the sequences in FIG. 2 reveals that they are composed of both hydrophobic amino acids and hydrophilic amino acids. When the sequence from the MN isolate is placed in a conformational template referred to as the helical wheel (FIG. 3), the peptide separates into a side that is composed mostly of hydrophobic amino acids and another side that is mostly hydrophilic amino acids. This demonstration of amphipathicity implies that, under ideal conditions such as those found surrounding the peptide in the intact protein, this stretch of amino acids has the capability of being α-helical. In addition, the diagram shown in FIG. 3 may shed light on the actual amino acids that are necessary for the peptide to bind to the CD4 receptor. The hydrophilic amino acids may be those exposed to the water interface of gp120 and, therefore, may comprise the epitope recognized by neutralizing antibodies.

Figure 4:
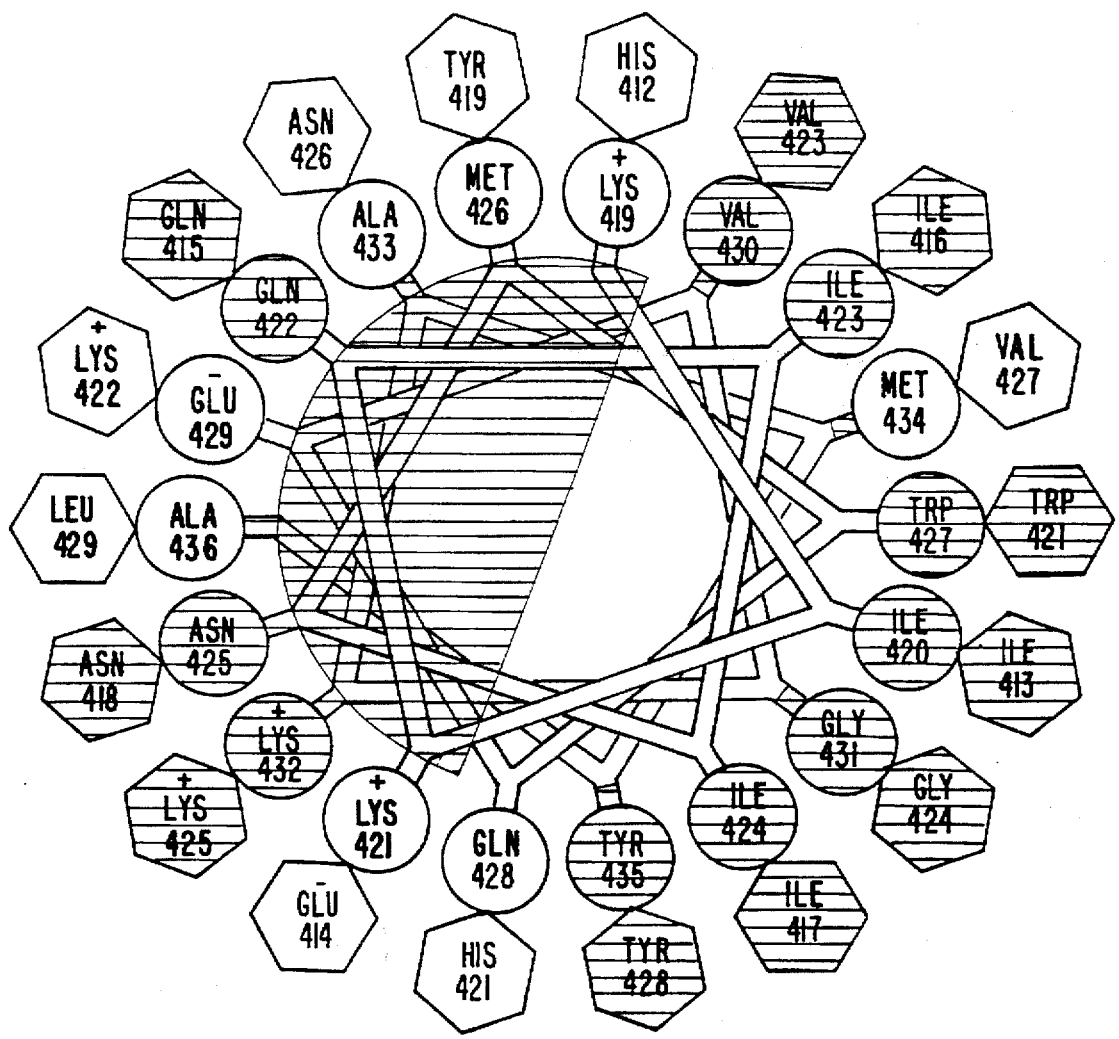
FIG. 4 shows residues 419-436 of gp120 from the MN isolate in a helical wheel along with residues from the ISYR isolate of HIV-2.

FIG. 4 is a helical wheel comparing the same region from the MN isolate to an HIV-2 sequence. Although the sequences show little sequence identity when compared linearly (see FIG. 2), the helical wheel reveals that the hydrophobic sides of the two helices differ by only two amino acid residues. This observation is particularly relevant because the hydrophobic side of the helix is thought to bind CD4.

Thus, synthetic analogues of these sequences from the CD4 binding region of gp120 of HIV-1 or HIV-2 should block binding so long as they maintain an α-helical secondary structure. The production and use of such analogues is described below.

A preferred method for obtaining a helical conformation is by construction of peptomers from desired oligopeptides, as described in detail below. The present invention also provides compositions comprising components which enhance the ability of the individual peptide monomers to form an α-helix. In particular, as shown in the Example section below, detergents, in particular nonionic detergents, enhance the ability of the of the peptide monomers to form an α-helix. Peptide monomers prepared in this way show enhanced binding to CD4.

Any of a number of detergents well known to one of skill in the art can be used in the compositions of the present invention. Suitable detergents include sodium laureate, sodium oleate, sodium lauryl sulfate, octaoxyethylene glycol monododecyl ether, octoxynol 9 and other detergents compatible with IV injection such as TWEEN® -80 (polyoxyethylene (20) sorbitan monooleate), n-octyl-β-D-glucopyranoside, and the like. Ionic detergents such as GAFAC® 560 (polyoxyethylene nonylphenyl ether phosphate), sodium dodecyl sulfate and the like are also suitable.

Construction of Peptomers of the invention

The peptomers of the present invention comprise repeating polypeptides (peptide monomers). The peptomers may be homopolymers consisting of a single repeating peptide monomer or alternatively may be heteropolymers consisting of two or more different repeating peptide monomers or subunits. In general the peptomers may consist of about 2 to about 100 peptide monomers, usually about 5 to about 50, preferably about 10 to about 20. Each peptide monomer may range in length from about 6 to about 40 amino acid residues, usually about 10 to about 30, preferably about 12 to about 20.

One of skill will recognize that the peptide monomers may be chemically synthesized or produced by means of recombinant genetics. Similarly, the peptomers may be produced by chemically linking peptide monomers together or alternatively the peptomer can be recombinantly expressed, although the peptomer is preferably produced by chemical linkage.

Methods for recombinant expression of desired polypeptides is well known in the art. The polypeptides (either peptide monomers or peptomers) may be expressed in a variety of prokaryotic or eukaryotic cells. Prokaryotic cells such as *E. coli* are typically preferred. Alternatively, eukaryotic systems such as mammalian, insect or yeast cells can be used. For a general description of methods suitable for the recombinant expression of desired polypeptides see, e.g., Sambrook et al, *Molecular Cloning—A Laboratory Manual*, Cold Spring Harbor Laboratory, Cold Spring Harbor, New York, 1989.

In a preferred embodiment the peptide monomers will be produced by chemical synthesis and then chemically polymerized to form a peptomer. Peptomers may be synthesized by a number of methods known to those of skill in the art. In general, peptomer synthesis involves synthesizing peptides (peptide monomers) that incorporate a reactive moiety that may be used to form a covalent linkage, either directly or through a linker, to another peptide monomer. Such reactive moieties may be naturally occurring, such as cysteine residues, or they may be non-natural, such as haloacetyl derivatized amino acids.

Linkers suitable for joining peptides are well known to those of skill in the art. Generally linkers are either hetero- or homo-bifunctional molecules that contain a two reactive sites that may each form a covalent bond with the respective peptide. A number of linker molecules are well known to those of skill in the art. For example, the peptide monomers may be joined by a peptide linker, by a straight or branched chain carbon chain linker, or by a heterocyclic carbon. Heterobifunctional cross linking reagents such as active esters of N-ethylmaleimide have been widely used. See, for example, Lerner et al. (1981) *Proc. Nat. Acad. Sci. (U.S.A.)*, 78: 3403–3407 and Kitagawa et al. (1976) *J. Biochem.* 79: 233–236.

In a preferred embodiment, the peptomers are synthesized by the methods disclosed in U.S. Pat. No. 5,066,716, copending and commonly assigned application U.S. Ser. No. 07/715,650, filed Jan. 14, 1991, and by Inman et al., (1991) *Bioconjugate Chem.* 2: 458–463. This method generally involves incorporating a haloacetyl group into a peptide monomer and then reacting that haloacetyl group with a free sulfhydryl group (or reactive amine) on another peptide monomer to form a covalent linkage between the monomers thereby creating a peptide polymer. The haloacetyl groups may be placed at any location within the polypeptide and react well with peptides containing sulfhydryl-bearing residues (e.g., cysteine). The peptide monomers are polymerized by reaction of the free sulfhydryl group on a residue in one peptide monomer with the haloacetyl group (e.g., bromoacetyl or chloroacetyl) of another peptide monomer to form covalently linked polymeric peptides referred to as peptomers.

When the peptomers of the invention are used as immunogens, they are preferably designed to avoid reactive groups such as free sulfhydryl groups or disulfide bonds in the final product. These groups can take part in disulfide exchange with sulfhydryl groups and disulfide bonds on host proteins in vivo and cause covalent linkages with host proteins. Thus, such compositions may inadvertently lead to immune responses against the modified host proteins. To avoid these problems, sulfhydryl groups and other reactive sites on the peptomers of the inventions are preferably destroyed. This may be accomplished by a number of methods well known to those of skill in the art. For instance, free haloacetyl groups can be removed by treatment of the peptomers with mercaptoethanol, and the like. Similarly, free sulfhydryl groups can be removed by treatment with iodoacetamide.

A) Synthesis of Peptide Monomers

Peptide monomers may be chemically synthesized by a number of means well known to those of skill in the art. Solid phase synthesis in which the C-terminal amino acid of the sequence is attached to an insoluble support followed by sequential addition of the remaining amino acids in the sequence is the preferred method for preparing the peptide monomers of the present invention. Techniques for solid phase synthesis are described by Barany and Merrifield,

*Solid-Phase Peptide Synthesis*; pp. 3–284 in *The Peptides: Analysis, Synthesis, Biology. Vol. 2: Special Methods in Peptide Synthesis, Part A.,* Merrifield, et al *J.* (1963) *Am. Chem. Soc.* 85: 2149–2156 and Gross and Meienhofer, eds. Academic Press, N.Y., 1980 and Stewart et al., Solid Phase Peptide Synthesis, 2nd ed. Pierce Chem. Co., Rockford, Ill. (1984).

Peptide monomers from the desired protein may be modified as necessary to provide a number of desired attributes, e.g., improved pharmacological characteristics, enhanced antigenicity, and the like. For instance, the peptides may be subject to various changes, such as substitutions, either conservative or non-conservative, where such changes might provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr.

The peptide monomers can also be modified by altering the order or composition of certain residues, it being readily appreciated that certain amino acid residues essential for biological activity, e.g., those critical to recognition by neutralizing anti-HIV antibodies may generally not be altered without an adverse effect on biological activity. The non-critical amino acids need not be limited to those naturally occurring in proteins, such as L-α-amino acids, or their D-isomers, but may include non-protein amino acids as well.

If haloacetyl chemistry is used to construct peptomers, choice of peptide synthesis chemistry is generally constrained by the requirement that the haloacetyl moieties are stable to the reaction conditions and environments used in the synthesis and deprotection of the peptide monomer. In a preferred embodiment, peptide synthesis is performed on an automated peptide synthesizer using t-BOC based chemistry.

Haloacetyl compounds may be incorporated into the peptide monomer at any location. Incorporation of the haloacetyl compound at the N terminus simply requires removal of the N-terminus protecting group (e.g. t-boc) and treatment with the haloacetic acid anhydride (see, U.S. Pat. No. 5,066,716). The completion of the reaction is determined by the absence of the free amine. The reaction rate can be monitored by the ninhydrin reaction of the resin according to the procedure of Sarin et al. (1981) *Anal. Biochem.* 117: 147–157.

Incorporation of the haloacetyl compound at any other location requires coupling of a modified amino acid. Thus, for example, $N^{\alpha}$-tert-butoxycarbonyl-$N^{\epsilon}$-(N-bromoacetyl-β-alanyl) -L-lysine (BBAL) may be used to place a bromoacetyl moiety at any position in the peptide monomer. See Robey et al. page 633–634 in 12th *Am. Peptide Symp.* Jun., (1992). Similarly, placement of a chloroacetyl moiety at any location within the peptide monomer may be accomplished using a chloroacetylated BBAL residue, U.S. Ser. No. 07/715,650.

Standard synthesis techniques are typically modified to account for the addition of the haloacetyl compound. The approach varies depending on the particular haloacetyl moiety and whether it is added internally to the peptide monomer or is placed in a terminal position. The details of synthesis of peptide monomers with terminal haloacetyl compounds may be found, for instance, in U.S. Pat. No. 5,066,716. The synthesis of peptide monomers with internal haloacetyl compounds may be found in Ser. No. 07/715,650.

The peptide can be cleaved and the protecting groups removed by either stirring the insoluble carrier or solid support in anhydrous, liquid hydrogen fluoride (HF) in the presence of anisole and dimethylsulfide at about 0° C. for about 20 to 90 minutes, preferably 60 minutes or by bubbling hydrogen bromide (HBr) continuously through a 1 mg/10 ml suspension of the resin in trifluoroacetic acid (TFA) for 30 to 60 minutes at about room temperature, depending on the protecting groups selected. Following ethyl acetate extraction of the residual peptide-resin mixture, the peptide monomer is extracted with 0.1M aqueous acetic acid, separated from the resin by filtration through a scintered glass filter and dried by lyophilization. Other deprotection methods well known to those of skill in the art may also be used. *Introduction to Cleavage Techniques. Strategies in Peptide Synthesis* (Applied Biosystems, Foster City Calif., 1990).

In general, the haloacetylated peptides may be used for polymerization reactions without purification. However, if desired, the peptide monomers may be purified using standard techniques such as high performance liquid chromatography (HPLC) using a $C_8$ column and a buffer system consisting of 0.1% trifluoroacetic acid/water/acetonitrile. Purification is generally performed under acetic conditions and low temperature (e.g., 0°—4° C.) to prevent reactions between the haloacetyl groups and the thiol groups in the peptide monomers.

By Polymerization of Monomers into Peptomers

In general if the monomers are to be directly linked together, polymerization requires reacting the monomers with each other in the presence of an activating or condensing agent to induce the formation of a covalent linkage between the reactive sites on the monomers. In a preferred embodiment, the reactive sites will be chosen to react spontaneously without requiring an activating agent. Where the monomers are linked with a linker, polymer construction may be carried out in a sequential manner, first coupling the linker to a first monomer and then coupling a second monomer to the bound linker and repeating the process for each monomer coupling step. Alternatively, the linkers and monomers may be simultaneously coupled. Where it is desired to produce a heteropolymer with subunits in a particular order, sequential polymerization is preferred.

Peptide monomers are generally capable of cyclization in addition to linear polymerization. Generally the tendency to cyclize may be controlled by regulating the concentration of peptide monomer in the reaction mixture. At high concentrations (e.g. 10 mg/ml or greater), predominantly linear peptomers will form, while at low concentrations (e.g. less than 1 mg/ml) peptomers will tend to cyclize.

In a preferred embodiment polymerization of a haloacetylated peptide monomer may be accomplished by simply reacting the monomer with a cysteine-bearing monomer in a phosphate or carbonate buffer at pH 7–8. The reaction progresses spontaneously without a condensing or activating agent.

Progress of the polymerization may be detected by titration of —SH groups with DTNB as described by Ellman (1959) *Arch. Biochem. Biophys.*, 82: 70–77. Alternatively polymerization may be evaluated by HPLC gel filtration or by SDS-PAGE (polyacrylamide gel electrophoresis), as described by Laemmli (1970) *Nature(London)* 227: 680–685 and staining with silver iodide or Coomassie brilliant blue.

C) Isolation/Purification of Peptomer

Where polymerization yields a pool of peptomers containing differing numbers of peptide monomers, it may be desired to isolate peptomers of a single length. This may be accomplished by a number of means of protein purification well known to those of skill in the art. These include, for example, gel electrophoresis, capillary electrophoresis, gel filtration, high performance liquid chromatography (HPLC), affinity chromatography, ion exchange chromatography, sizing chromatography or other protein purification techniques well known to those of skill in the art. See, for instance, Scopes, *Protein Purification: Principles and Practice*, Springer-Verlag: N.Y. (1982) and *Methods in Enzymology Vol. 182: Guide to Protein Purification.*, Deutscher, ed. Academic Press, Inc. N.Y. (1990).

D) Secondary Structure of Peptomers

As noted above, in certain preferred embodiments the secondary structure of the peptomers will closely approximate the α-helical structure of the native protein. The sequence of the individual peptide monomers is selected so that the peptomer is amphipathic and the location of hydrophobic and hydrophilic residues favors an α-helical structure (see, e.g., Kamtekar et al., (1993) *Science* 262: 1680.

The degree of α-helicity of a peptomer of the invention can be determined using standard techniques, such as circular dichroism spectroscopy (see, e.g., Provencher et al., (1981) *Biochem.* 20: 33–37). Using this technique, the peptomers of the invention usually show considerably more α-helical character than the peptides from which they are derived. Typically, the degree of α-helical character of the peptomers is at least about 20%, usually greater than about 30%, and in certain embodiments, greater than about 50%.

Use of Peptomers in Immunoassays

The invention also provides methods for detecting infection, monitoring the progression of disease or the efficacy of treatment by detection of conformational epitopes on antigens, e.g., anti-gp120 antibody levels in serum or other bodily fluids such as urine, saliva, cerebrospinal fluid, semen, and the like. For a review of the general procedures for performing assays of the invention, see *Basic and Clinical Immunology* 7th Edition (D. Stites and A. Terr ed.) 1991.

The assays can be either competitive or noncompetitive. In competitive binding assays, the sample analytes (e.g., target anti-gp120 antibodies) compete with a labeled analyte (labeled anti-gp120 antibodies) for specific binding sites on a capture agent (a peptomer comprising peptides from gp120) bound to a solid surface. The concentration of labeled analyte bound to the capture agent is inversely proportional to the amount of free analyte present in the sample.

Noncompetitive assays are typically sandwich assays, in which the sample analyte (target anti-gp120 antibody) is bound between two analyte-specific binding reagents. One of the binding agents is used as a capture agent and is bound to a solid surface. The other binding agent is labelled and is used to measure or detect the resultant complex by visual or instrument means.

A number of combinations of capture agent and labelled binding agent can be used. For instance, a peptomer comprising gp120 peptides can be used as the capture agent and labelled anti-human antibodies specific for the constant region of human antibodies can be used as the labelled binding agent. Goat, sheep and other non-human antibodies specific for human immunoglobulin constant regions (eg. γ or μ) are well known in the art. Alternatively, the anti-human antibodies can be the capture agent and the peptomer can be labelled.

Other proteins capable of specifically binding human immunoglobulin constant regions, such as protein A or protein G may also be used as the capture agent or labelled binding agent. These proteins are normal constituents of the cell walls of streptococcal bacteria. They exhibit a strong non-immunogenic reactivity with immunoglobulin constant regions from a variety of species. See, generally Kronval, et al. (1973) *J. Immunol.*, 111: 1401–1406, and Akerstrom, et al. (1985), *J. Immunol.*, 135: 2589–2542.

The non-competitive assays need not be sandwich assays. For instance, the antibodies in the sample can be bound directly to the solid surface. The presence of antibodies to the target microorganism in the sample can then be detected using labelled antigen.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5: 34–41).

Some assay formats do not require the use of labelled components. For instance, agglutination assays can be used to detect the presence of the target antibodies. In this case, peptomer-coated particles are agglutinated by samples comprising the target antibodies. In this format, none of the components need be labelled and the presence of the target antibody is detected by simple visual inspection.

As mentioned above, depending upon the assay, various components, including the peptomer, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC or polystyrene) or a bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system. In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a component of the assay and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See for example Immobilized Enzymes, Ichiro Chibata, Halsted Press, N.Y., 1978, and Cuatrecasas (1970), *J. Biol. Chem.* 245: 3059.

In addition to covalent bonding, various methods for noncovalently binding an assay component can be used. Noncovalent binding is typically nonspecific absorption of a compound to the surface. Typically, the surface is blocked with a second compound to prevent nonspecific binding of labelled assay components. Alternatively, the surface is designed such that it nonspecifically binds one component but does not significantly bind another. For example, a surface bearing a lectin such as Concanavalin A will bind a carbohydrate containing compound but not a labelled protein that lacks glycosylation. Various solid surfaces for use in noncovalent attachment of assay components are reviewed in U.S. Pat. Nos. 4,447,576 and 4,254,082.

Many assay formats employ labelled assay components. The labelling systems of the invention can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3$H, $^{125}$I, $^{35}$S, $^{14}$C, or $^{32}$P labelled compounds or the like. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904.

In another aspect, the present invention can be provided in a kit format for detecting anti-gp120 antibodies. Such a kit includes peptomers specifically recognized by the target antibodies and a labelling system, including enzyme substrates and the like, suitable for detecting the immune complexes formed by the peptomers and target antibodies. The kits also include appropriate washing solutions, dilution buffers and the like for preparation and analysis of urine samples.

Immunogenic and Pharmaceutical Compositions

The peptomers of this invention may also be used as immunogens to produce antibodies against target proteins, such as gp120. An amount adequate to accomplish this is defined here as an "immunogenically effective dose". For instance, the peptomers of the invention can be used to raise monoclonal or polyclonal antibodies that can be used to detect the presence of HIV. Antibodies which bind peptomers of the invention may be produced by a variety of means. The production of non-human monoclonal antibodies, e.g., murine, lagomorpha, equine, etc., is well known and may be accomplished by, for example, immunizing the animal with an immunogenic composition containing the polypeptide. Antibody-producing cells obtained from the immunized animals are immortalized and screened, or screened first for the production of antibody which inhibits binding between gp120 and CD4 and then immortalized. For a discussion of general procedures of monoclonal antibody production see Harlow and Lane, *Antibodies, A Laboratory Manual* Cold Spring Harbor Publications, N.Y. (1988) and Antibodies in Cell Biology, Asai, D., ed. (Academic Press, San Diego, Calif., 1993).

As shown below, the immunogenic composition used to raise antibodies is preferably selected so as to preserve the secondary structure of the peptomer. Preservation of the secondary structure is thought to maintain conformational epitopes in the peptomer. As shown below, oil based, lipophilic adjuvants such as Freund's adjuvant, do not preserve the structure in a form that is recognized by antibodies that are also reactive with the native protein. Thus, preferred adjuvants are aqueous solutions such as Ribi's adjuvant, which contains three components extracted from bacteria, monophosphoryl lipid A, trehalose dimycolate and cell wall skeleton (MPL+TDM+CWS) in a 2% squalene/Tween 80 emulsion. Other suitable adjuvants include alum, aluminum phosphate, aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), and N-acetylmuramyl-Lalanyl-D-isoglutaminyl-L-alanine-2-(1'-2'-dipalmitoyl-sn-glycero-3-hydroxyphosphoryloxy)-ethylamine (CGP 19835A, referred to as MTP-PE). The effectiveness of an adjuvant may be determined by measuring the amount of cross-reactive antibodies directed against the immunogenic peptomer.

The compositions of the invention can also be administered prophylactically or to an individual already suffering from a disease. Thus, the invention also provides pharmaceutical compositions which are suitable for administration to humans, to treat and/or prevent disease, such as AIDS. Suitable formulations for this purpose are well known to those of skill in the art and can be found, for instance, in *Remington's Pharmaceutical Sciences*, Mack Publishing Company, Philadelphia, Pa., 17th ed. (1985).

The pharmaceutical compositions can be administered to a patient in an amount sufficient to elicit a therapeutic or protective immune response against the target antigen, such as HIV envelope proteins. Alternatively, the peptomers can be used to directly block interaction of a disease organism with human cells. In the case of HIV infection, the peptomers should block interaction of the virus with CD4 on the surface of T cells and thus ameliorate symptoms of the disease. An amount adequate to accomplish this is defined as a "therapeutically effective dose."Amounts effective for this use will depend on, e.g., the peptomer composition, the manner of administration, the stage and severity of the HIV infection being treated, the weight and general state of health of the patient, and the judgment of the prescribing physician. For use as an immunogen, the peptomers are administered in doses which generally range for the initial immunization (that is for therapeutic or prophylactic administration) from about 0.01 mg to about 2.0 mg per 70 kilogram patient, more commonly from about 0.1 mg to about 1.0 mg per 70 kg of body weight. Boosting dosages are typically from about 0.1 mg to about 1.0 mg of peptomer using a boosting regimen over weeks to months depending upon the patient's response and condition. A suitable protocol would include injection at time 0, 3, 9, 24 and 52 weeks, followed by booster injections.

When the peptomers of the invention are used to block interaction of gp120 and CD4, they are preferably prepared using methods which preserve or enhance the solubility of the peptomer. For instance, if the peptomer is prepared using the haloacetyl chemistry described above, the final product is preferably not lyophilized. In the absence of a lyophilization step, the peptomers remain more soluble in aqueous solutions (typically solubility at least about 1mg/ml, preferably at least about 2mg/ml) and have increased ability to block binding (see, Example 7). In contrast, immunogenic compositions usually comprise relatively insoluble formulations (typically solubility less than about 1 mg/ml) to increase immunogenicity.

The peptomers of the invention can be used alone or in combination with other therapeutic agents such as subunit vaccines, in which case they may be used to enhance the immune response against desired regions of the antigen. For instance, the peptomers of the invention with increased solubility (e.g., prepared without a lyophilization step) can be used in combination with formulations that provide enhanced immunogenicity. Thus, such compositions can be used to directly block gp120-CD4 binding as well as elicit an anti-gp120immune response. In other embodiments, a peptomer derived from the CD4 binding region of gp120 can be used in combination with a gp120 or gp160 vaccine, to ensure that antibodies to the CD4 binding region are produced. Alternatively, the peptomer can be used in a boosting regimen to boost the immune response against this region.

It must be kept in mind that the pharmaceutical compositions of the present invention may be employed in serious disease states, that is, life-threatening or potentially life threatening situations. In such cases, in view of the minimization of extraneous substances and the relative nontoxic nature of the peptomers of the invention, it is possible and may be felt desirable by the treating physician to administer substantial excesses of these compositions.

For therapeutic use, administration should begin at the first sign of HIV infection. This is followed by boosting doses until viral load is substantially reduced or eliminated and for a period thereafter. In some circumstances, loading doses followed by boosting doses may be required. Vaccine compositions containing the peptides are administered prophylactically to a patient at risk of HIV infection to elicit an immune response against the virus.

The pharmaceutical compositions are intended for parenteral or oral administration. Preferably, the pharmaceutical compositions are administered parenterally, e.g., subcutaneously, intradermally, or intramuscularly. Thus, the invention provides compositions for parenteral administration which comprise a solution of the peptomers dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophiized, the lyophilized preparation being combined with a sterile solution prior to administration. The compositions may contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, and the like.

When peptomers of the invention are used to block CD4 binding, they are preferably used in compositions useful in preventing an initial viral infection at the point of entry into the body. Since HIV is sexually transmitted, the peptomers are conveniently included in compositions applied in the urogenital tract. For instance, such peptomers can be used with condoms or spermicidal gels.

For solid compositions, conventional nontoxic solid carriers may be used which include, for example, pharmaceutical grades of alumina, mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptomers of the invention, and more preferably at a concentration of 25%–75%.

As noted above, in some embodiments, the compositions are intended to induce an immune response against the peptomers. Thus, compositions and methods of administration suitable for maximizing the immune response are preferred. Useful carriers are well known in the art, and include, e.g., thyroglobulin, albumins such as human serum albumin, tetanus toxoid, polyamino acids such as poly (lysine:glutamic acid), influenza, hepatitis B virus core protein, hepatitis B virus recombinant vaccine and the like. In addition, adjuvants, as described above, may also be included.

The concentration of peptomers of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

The following examples are provided to illustrate, but not to limit the present invention.

EXAMPLE 1

Synthesis of Specific Peptomer a) Synthesis of the (419-436) peptide monomer

The N-bromoacetyl peptide sequence, N- KIKQIINM-WQEVGKAMYA -C corresponding to residues 419 to 436 of the HIV-1 glycoprotein (gp120), was synthesized using an automated solid phase peptide synthesizer (Model 430A, Applied Biosystems, Foster City, Calif., U.S.A.). As a last step in synthesis, bromoacetic acid was reacted with the amino terminal amino acid to form the N-bromoacetyl-derivatized fully protected peptide (peptide monomer). This was carried out simply by substituting 2.0 mmol of bromoacetic acid for glycine in an empty glycine cartridge as the last step in the synthesis and using the programmed run file of the automated synthesizer for the glycine coupling. Bromoacetic acid anhydride (1.0 mmol) is formed as an intermediate in the coupling reaction done on a 0.5 mmol scale.

Deprotection and release of the bromoacetylated peptide from the PAM resin was accomplished by treating the resin with anhydrous hydrofluoric acid containing 10% anisole at 0 C. for 2 hours. Following ethyl acetate extraction of the residual peptide-resin mixture, the peptide was extracted with 0.1 M aqueous acetic acid, separated from the resin by filtration through a scintered glass filter, and dried by lyophilization. The crude peptide was obtained in a yield of approximately 95%. If necessary the peptides can be further purified prior to polymerization using standard techniques, such as HPLC.

b) Polymerization of the peptide monomers to form peptomer (419-436) The peptide polymers were prepared by dissolving 5 mg of the N-bromoacetyl cysteine-containing peptides in 1.0 ml of deoxygenated 0.5M $NaHCO_3$ or 0.1M $NaHPO_4$, pH 7.0-7.5 buffer and stirring these solutions under $N_2$ for 5-12 hours at 25° C. The resulting peptomers are generally only partially soluble water and not soluble in buffered saline solutions. They are soluble in 10% acetic acid at less than about 1mg/ml.

EXAMPLE 2
Immune Response of Peptomer (419-436) in Rabbits

Rabbits were initially immunized with peptomer (419-436) in Freund's Complete Adjuvant followed by a single boost with Freund's Incomplete Adjuvant. In only 2 or 3 weeks there was a titer of 1:10,0000 for the antibody binding to the peptomer. However, the antibody was not able to recognize gp120 or to neutralize HIV-1 infection in vitro. While the reasons for this are not entirely understood, it is suspected that since Freund's adjuvants are composed mostly of mineral oil the peptide is unable to retain its native conformation. Freund's adjuvants are extremely non-polar. Therefore a peptide that depends on hydrophobic interactions to maintain its conformation may change its conformation in Freund's, thereby losing its activity.

Rabbits were then immunized with 1 mg of peptomer (419-436) in Rib's adjuvant and the response is shown in Table 1. After 9 weeks, the titer against the peptomer was approximately 1:3,200.

HIV-1 MN isolate was neutralized at a dilution of 1:70. Neutralization assays were carried as described in Robert-Guroff, et al. in *Techniques in HIV Research* Aldovini and Walker eds. pp. 179-185 (Aldrich 1990).

The antibodies also reacted well with recombinant soluble gp120 in a dot blot assay. The dot blot assays were carried as follows. Peptomers in $H_2O$ were spotted onto nitrocellulose paper. The nitrocellulose was then blocked with 3% bovine serum albumin in tris-buffered saline (TBS) pH 7.4 for 1 hour, then treated with 1 µg/ml biotinylated rsCD4 (Genentech, South San Francisco, Calif.) for 3 hours in a buffer containing TBS and 0.1% Tween 20. The nitrocellulose was then treated with a 1:750 dilution of streptavidin-horseradish peroxidase conjugate and developed. Together these results strongly suggest that the antibodies bind to gp120 and prevent HIV-1 from binding and infecting CD4-bearing cells.

TABLE 1

Immune Response of Rabbits to Peptomer (419-436).

| Adjuvant | 3 Week Titer | 9 Week Titer | gp120 Reactivity | Neutralization |
|---|---|---|---|---|
| Freund's | 1:10,000 | 1:20,000 | 0 | None |
| Ribi's | 1:3,200 | 1:6,400 | ++ | 1:15 to 1:70 | gp120 Reactivity was in the dot blot assay. Neutralization was with an in vitro neutralization assay using the MN isolate of HIV-1.

EXAMPLE 3
Immune Response of Peptomer (419-436) in Rhesus Monkeys

This experiment was done with Rhesus monkeys that had been primed with various attenuated poxvirus recombinant carrying HIV-1$_{MN}$ genes and boosted with envelope and gag proteins formulated in alum. Six monkeys were used for the studies. Two of the monkeys were immunized with peptomer(419-436) suspended in phosphate-buffered saline (PBS at pH 7.4 without adjuvant) and four were immunized with peptomer(419-436) in alum. Each animal was injected with a single 1 ml bolus containing 1 mg peptomer(419-436) in a subscapular location in order that the immunogen be administered in a lymph node-rich locus. Three weeks after the initial injection, the monkeys were injected again and the final evaluation was performed after an additional three weeks (a total of six weeks from the initial injection).

The peak neutralization titers, for all monkeys, which ranged from 40 to 650 during previous immunizations had declined to low levels prior to administration of the peptomer (Table 2). Monkey 236L who achieved the highest neutralization titers of 620, had a titer of 25 at the time of immunization with the peptomer.

Three weeks following the initial administration of the peptomer(419-436) an ELISA titer against the peptomer of 1:3,200 was detected for the monkeys immunized with peptomer in alum. No titer was detected for those monkeys immunized with peptomer in PBS. The monkeys were boosted and three weeks later, the monkeys who received peptomer in alum all had a titer equal to about 1:6,400 compared to 1:1,600 for the monkeys who received peptomer in PBS.

The neutralization titers of the peptomer/PBS-immunized monkeys increased from 0 to about 1:40-1:50. The same appeared for the alum-containing immunogen. However, one monkey in this group did not respond to any immunogen including the poxvirus/subunit cocktails administered before these studies.

TABLE 2

Immune Response of Rhesus Monkeys to Peptomer (419-436).

| I.D. | | ELISA titer | | HIV-1 (MN) NEUTRALIZATION | |
|---|---|---|---|---|---|
| No. | Adjuvant | 0 weeks | 6 weeks | 0 weeks | 6 weeks |
| 235L | PBS | 0 | 1;1,600 | — | 40 |
| 236L | PBS | 0 | 1:3,200 | 25 | 50 |
| 242L | Alum | 0 | 1;6,400 | — | 40 |
| 243L | Alum | 0 | 1;6,400 | — | 115 |
| 244L | Alum | 0 | 1;6,400 | 65 | 75 |
| 245L | Alum | 0 | 1:3,200 | — | — |

The neutralization titers are given as the reciprocal of the dilution of serum that gives a 40% neutralization of HIV-1 (MN) infection in vitro. A negative value means neutralization was not observed at the lowest serum dilution tested (1:25). The MN isolate was used because this was the strain used to design the peptomer.

Sera taken prior to the immunizations from monkeys that ultimately achieved the highest neutralization titers were tested for reactivity with the peptomer in an ELISA format. No reactivity was observed. Thus, all of the monkeys, prior to receiving peptomer as an immunogen, did not produce antibodies to this region of gp120. After immunization with the peptomer, the monkeys did show a strong response in the ELISA. Thus a new epitope appeared due to the administration of the peptomer and the resulting boost in the in vitro neutralization was not a boost to a previous-existing titer but a new class of protective antibodies induced by the peptomer as an immunogen.

In summary, peptomer(419-436) is immunogenic in Rhesus monkeys previously immunized with various HIV-related immunogens including gp160/120. Furthermore, it appears that peptomer(419-436) is immunogenic alone and does not require an adjuvant. This may be due to the ability of the peptomer to bind to CD4 in the monkey and this may signal the immune system to respond by producing antibodies.

EXAMPLE 4
Immune Response of Peptomer(419-436) in Chimpanzees

Chimpanzees provide a good model system for testing the safety and efficacy of an antigenic material prior to human studies. Four chimpanzees that have never been used in any other trial are used in this study. The chimpanzees are divided into two groups with two chimpanzees in each group. Approximately 50 ml of whole blood are obtained from each chimpanzee. The blood is clarified and clotted to provide sera which is used throughout the experiment as the "pre-bleed" control. The original sera are divided into 0.1 ml aliquots which are stored at −70° C and which are used once after thawing. All evaluations are referenced to these controls.

On the first day following the prebleed, each animal, under ketamine anesthesia, is injected under the scapula (shoulder blade) with a suspension consisting of 1 mg peptomer (419-436) in 1 ml adjuvant. Each group of two chimpanzees receives the peptomer, but one group receives the peptomer in alum as adjuvant and the other with Ribi's adjuvant.

The chimps are allowed to rest for three weeks after which time, under ketamine anesthesia, they are bled of 20 ml and re-immunized in the exact same fashion as on the first day. At this point, the sera obtained are tested for antibodies against the peptomer, antibodies that react with gp120 and antibodies that block HIV-1 infection in vitro. The chimpanzees are then allowed to rest for six weeks and, after this time, a 20 ml bleed is taken. The chimpanzees are then immunized again as on day 1. The sera are again tested for the presence of anti-peptomer, anti-gp120 and neutralizing antibodies.

After 21 weeks, 20 ml bleeds are obtained to test for the titers of the antibodies. At this time, depending on antibody titer, the chimpanzees are either boosted as above or and then another test bleed is taken two weeks later, or nothing is done.

After a period of 6 months expires, another 20 ml test bleed is taken and the possibility of boosting the chimps again is evaluated. If necessary, the animals are boosted again. If the titers appear suitable, the chimpanzees are returned to their normal living environment with other chimpanzees and periodically observed for health and behavioral effects.

When in vitro neutralization titers believed to be protective are achieved (e.g., titers of 320–640), the chimpanzees are challenged with HIV-1 or HIV-2. The challenges is initially performed with the virus homologous to that used to produce the peptomer. Unrelated and untreated chimpanzees are used as a negative control. The onset of symptoms characteristic of HIV (e.g. reduced $CD^4$ + T cells) is then assayed in the treated and the untreated chimpanzees.

EXAMPLE 5
Secondary structure of peptomer(419-436)

Figure 5:
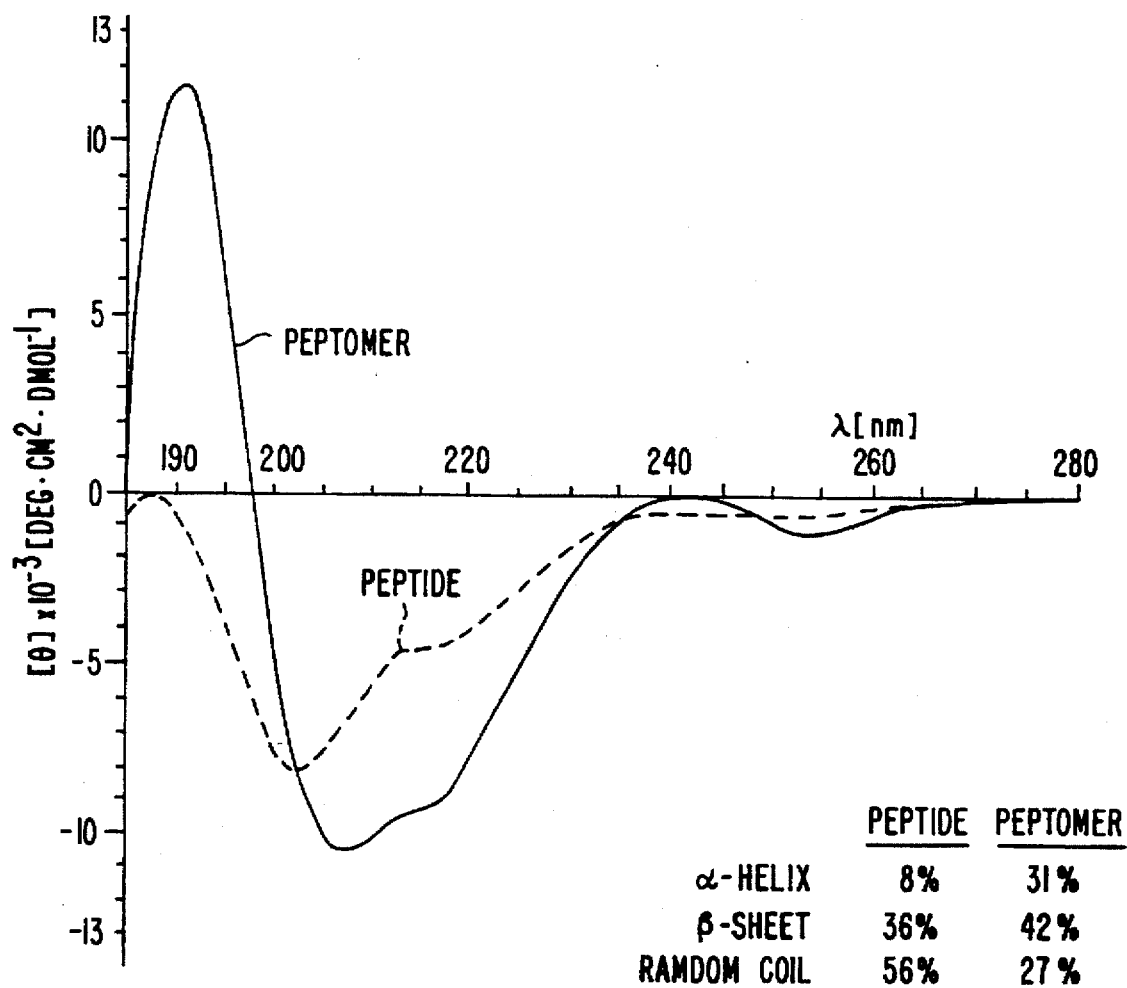
FIG. 5 shows the circular dichroism spectra of both the peptide and the peptomer(419-436).

Circular dichroism spectroscopy was used to determine the degree of α-helicity of the peptomer and the peptide from which it was derived. FIG. 5 shows the circular dichroism spectra of both the peptide and the peptomer(419-436). It is clear from the two spectra that they are considerably different and analyzing the data according to the methods of Provencher et al., (1981) *Biochem.* 20: 33–37, indicates that the peptomer contains far more α-helical character than the peptide itself. In this case, the peptide contains 8±7% helix, while the peptomer has 31±1%. This establishes that by polymerizing the peptide, the peptomer achieves a conformation that is not favored for the free peptide monomer.

EXAMPLE 6

Peptomer(419-436) is recognized by antisera from HIV infected individuals, while the corresponding peptide is not.

Standard ELISA methods were used in these experiments. Briefly, 96-well polystyrene plates were coated with 1 μg/well of peptide or peptomer. The results are presented in Table 3. The peptide found 9/27 (33%); the peptomer found 26/27 (96%); 1/10 (10%) false positive with the peptomer.

TABLE 3

ELISA Titers of HIV-1(+)
Serum Samples: Peptide 419–436 vs. Peptomer

| Sample No. | Diagnosis | Peptide 419–436 | Peptomer |
|---|---|---|---|
| 571 | HIV+ | 0 | 1:1280 |
| GSF2 | AIDS | 1:1280 | 1:1280 |
| LYM03 | Hodgkins | 0 | 0 |
| 863 | HIV+ | 0 | 1:1280 |
| GSF3 | AIDS | 1:1280 | 1:1280 |
| GSF1 | AIDS | 0 | 1:1280 |
| EYE01D | Uveitis | 0 | 0 |
| SF53 | AIDS | 0 | 1:1280 |
| 797 | HIV+ | 0 | 1:1280 |
| 770 | HIV+ | 0 | 1:640 |
| 217 | HIV+ | 0 | 1:640 |
| 156 | AIDS | 0 | 1:1280 |
| 196 | HIV+ | 0 | 1:1280 |
| 466 | HIV+ | 0 | 1:1280 |
| 555 | HIV+ | 0 | 1:1280 |
| 37 | HIV+ | 0 | 0 |
| GS46 | AIDS | 0 | 1:1280 |
| LYM02 | LYMPHOMA | 0 | 0 |
| 552 | HIV+ | 1:1280 | 1:1280 |
| EYE08C | VEITIS | 0 | 0 |
| LYM06 | LYMPHOMA | 0 | 0 |
| EYE06C | UVEITIS | 0 | 1:1280 |
| GS52 | AIDS | 1:640 | 1:1280 |
| 864 | HIV+ | 1:1280 | 1:1280 |
| 265 | HIV+ | 1:1280 | 1:1280 |
| 656 | HIV+ | 1:1280 | 1:1280 |
| 80 | AIDS | 0 | 1:1280 |
| 685 | HIV+ | 1:1280 | 1:640 |
| GS47 | AIDS | 0 | 1:320 |
| 865 | HIV+ | 1:320 | 1:1280 |
| KD15 | Kidney Graft | 0 | 0 |
| 589 | HIV+ | 0 | 1:1280 |
| 862 | HIV+ | 0 | 1:640 |
| 517 | HIV+ | 0 | 1:1280 |
| 740 | NORMAL | 0 | 0 |
| LYM-1 | LYMPHOMA | 0 | 0 |
| 7H8 | Kidney Graft | 0 | 0 |

EXAMPLE 7

Inhibition of binding of by peptomer 419-436.

The peptomer used in the experiments described in this Example was prepared without a lyophilization step. Thus, the peptide showed increased solubility in aqueous solutions and had enhanced ability to block binding between CD4 and gp120.

A. Inhibition of biotinylated CD4 binding to peptomer (419-436) by recombinant soluble gp120. Biotinylated CD4 was made by reacting 1.0 mg recombinant soluble CD4 (Genentech) with 15 mg. Biotin succinimide (Pierce Chem. Co.) in 0.1M sodium bicarbonate for 30 min. Following dialysis at 4° C. for 2 days into phosphate-buffered saline, the biotinylated CD4 was stored at 1 mg/ml at 4° C.

Figure 6:
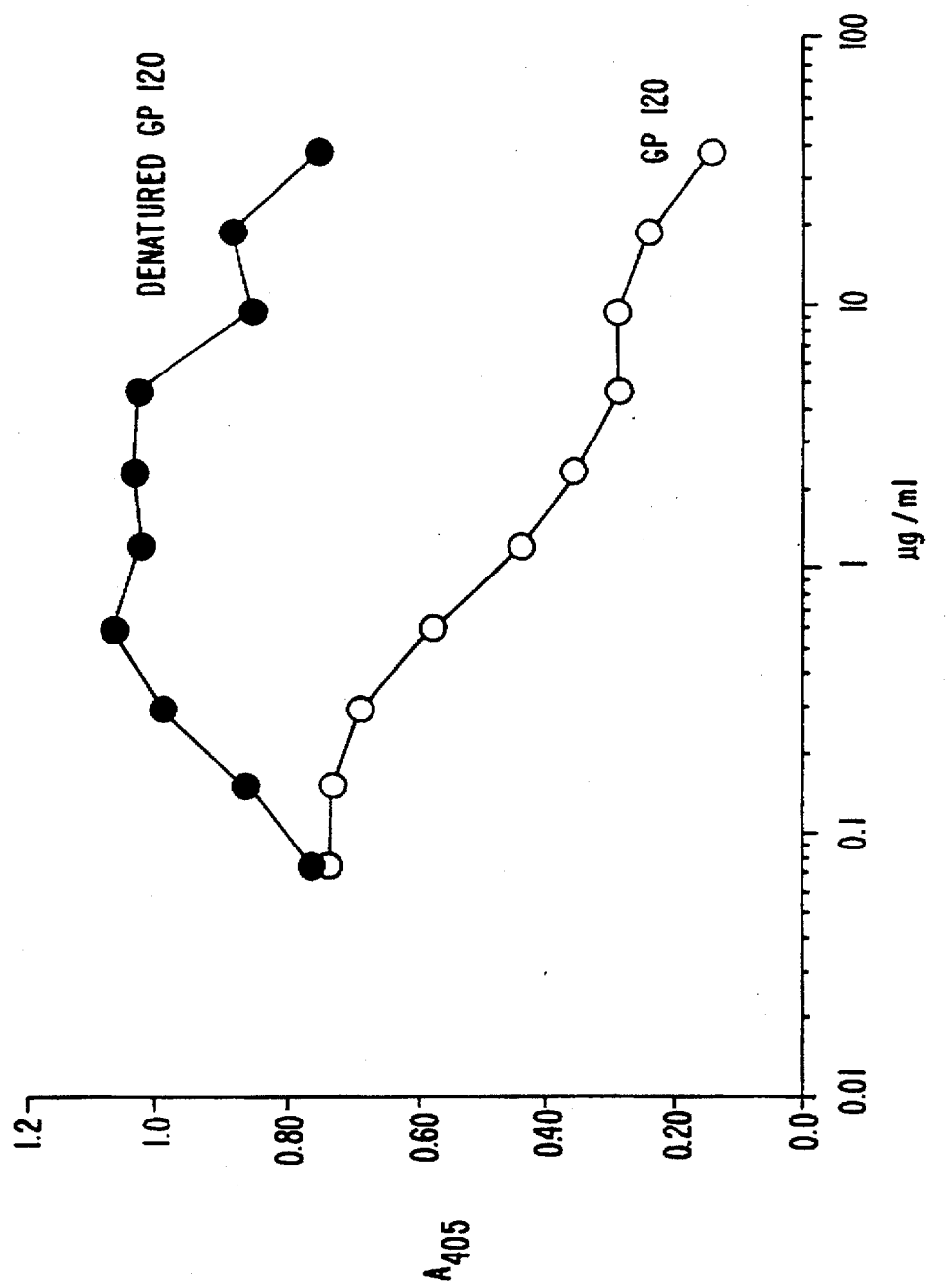
FIG. 6 shows inhibition of CD4 binding to peptomer(419-436) by recombinant soluble gp120. Open circles - recombinant gp 120. Closed circles-denatured recombinant gp 120.

To measure the inhibition of CD4 binding to peptomer (419-436) the following ELISA procedure was used: 10 μg/200 μl of the peptomer in PBS were used to coat the wells of a microtitre plate for 1 hr at room temperature. 1μg/well biotinylated CD4 was used. The amount of gp120 (native and denatured) used in the assay is shown in FIG. 6. The gp120 was denatured by SDS and beta mercaptoethanol. The biotin was detected with streptavidin-alkaline phosphatase Tago, Inc. (Burlingame, Calif.) at a dilution of 1:1000 and developed with p-nitrophenylphosphate.

Figure 7:
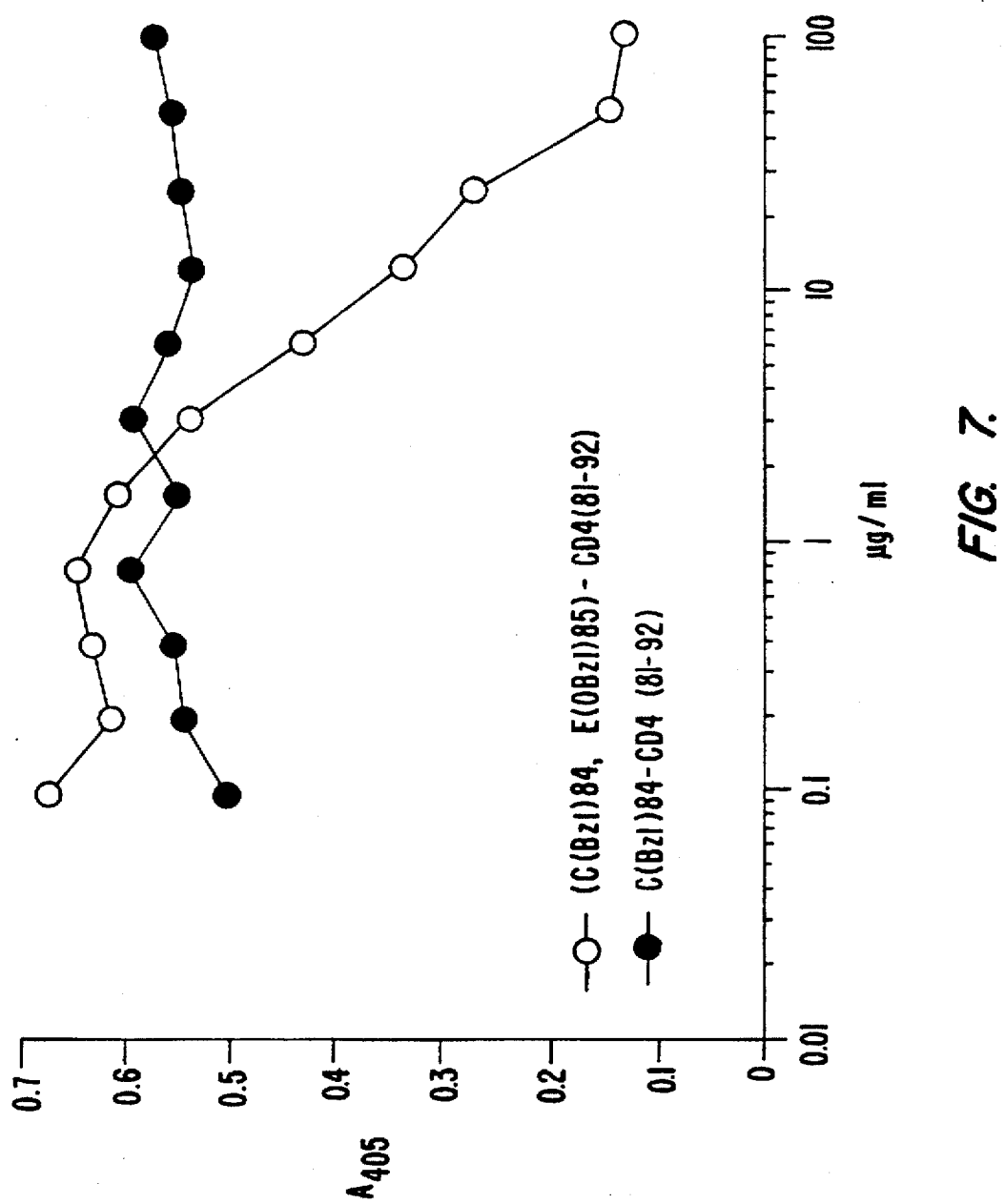
FIG. 7 shows inhibition of the binding of biotinylated CD4 to peptomer(419-436) by benzylated CD4-derived peptides.

B. Inhibition of the binding of biotinylated CD4 to peptomer(419-436) by benzylated CD4-derived peptides. Using the same ELISA procedure described above, the ability of benzylated CD4-derived peptides to block binding to peptomers of the invention was shown (FIG. 7). The benzylated peptides are were prepared as described by Lifson, et al. *AIDS Res. Hum. Retro.* 7: 521–527 (1991).

Figure 8:
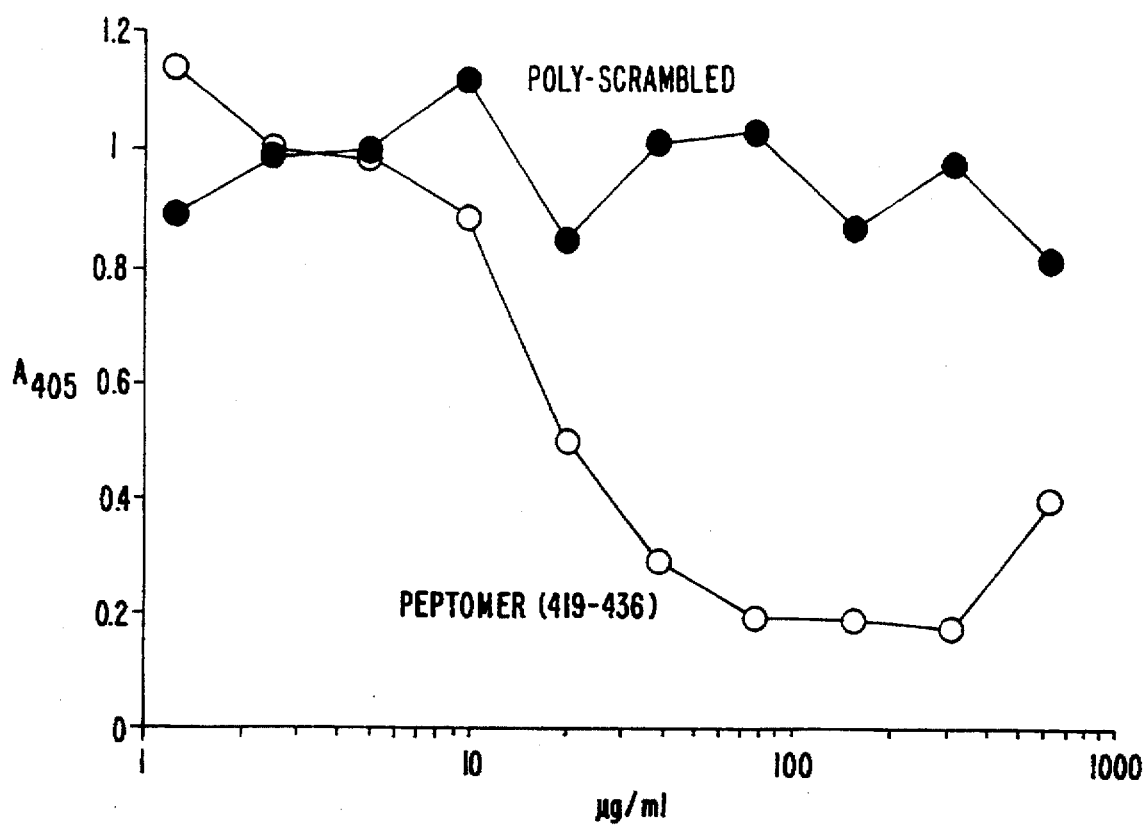
FIG. 8 shows inhibition of gp120binding to CD4 by peptomer(419-436).

C. Inhibition of gp120 binding to CD4 by peptomer(419-436). The ELISA procedure was the same as above except that 500 ng/well of recombinant soluble gp120 was used to coat each well instead of peptomer. Poly-scrambled peptomer is a peptomer that contains all the amino acids as in peptomer(419-436) in a scrambled order. Results are shown in FIG. 8.

Figure 9:
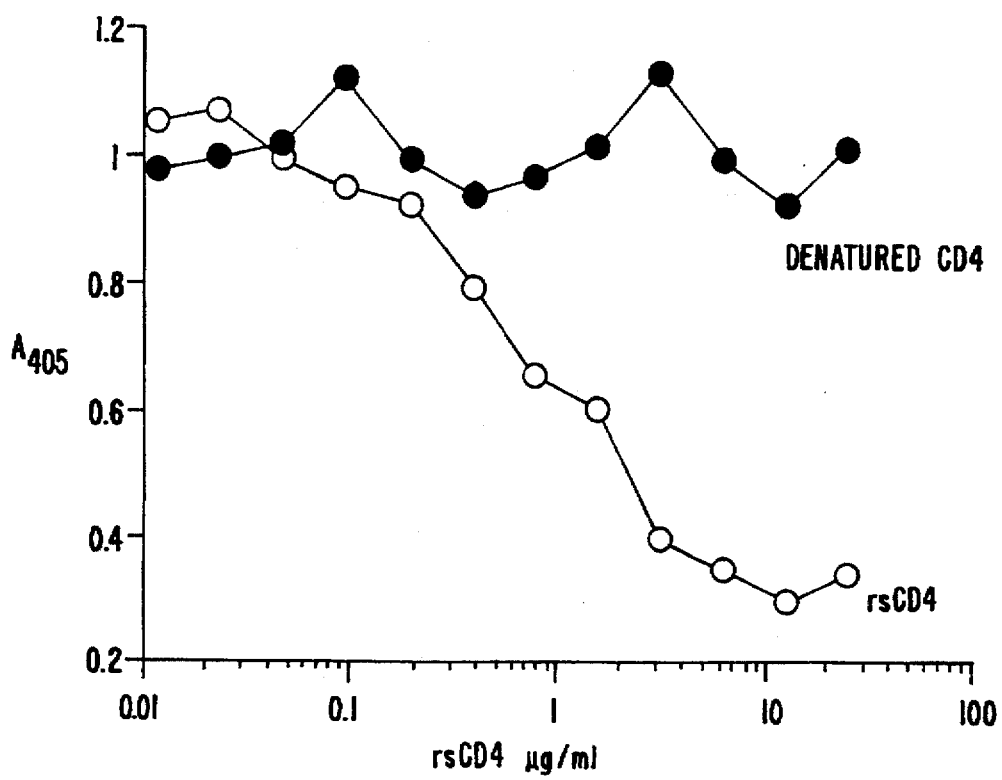
FIG. 9 shows inhibition of the binding of biotinylated CD4 to peptomer(419-436) by recombinant soluble CD4.

D. Inhibition of the binding of biotinylated CD4 to peptomer(419-436) by recombinant soluble CD4. The conditions of the ELISA are the same as in A, above. Results are shown in FIG. 9. The value of the inhibition at 50% is equal to about 1 µg/ml. This is the inhibition constant and is equal to approximately 24 nM. 24 nM is in close proximity to that value reported in the literature for binding gp120 to CD4 which ranges from 1 nM to 45 nM.

These results demonstrate that the peptomers of the invention can act as blockers of gp120 CD4 binding and thus inhibit infection of T cells by HIV.

EXAMPLE 8

Peptide monomers form α-helix in the presence of detergent

Figure 10:
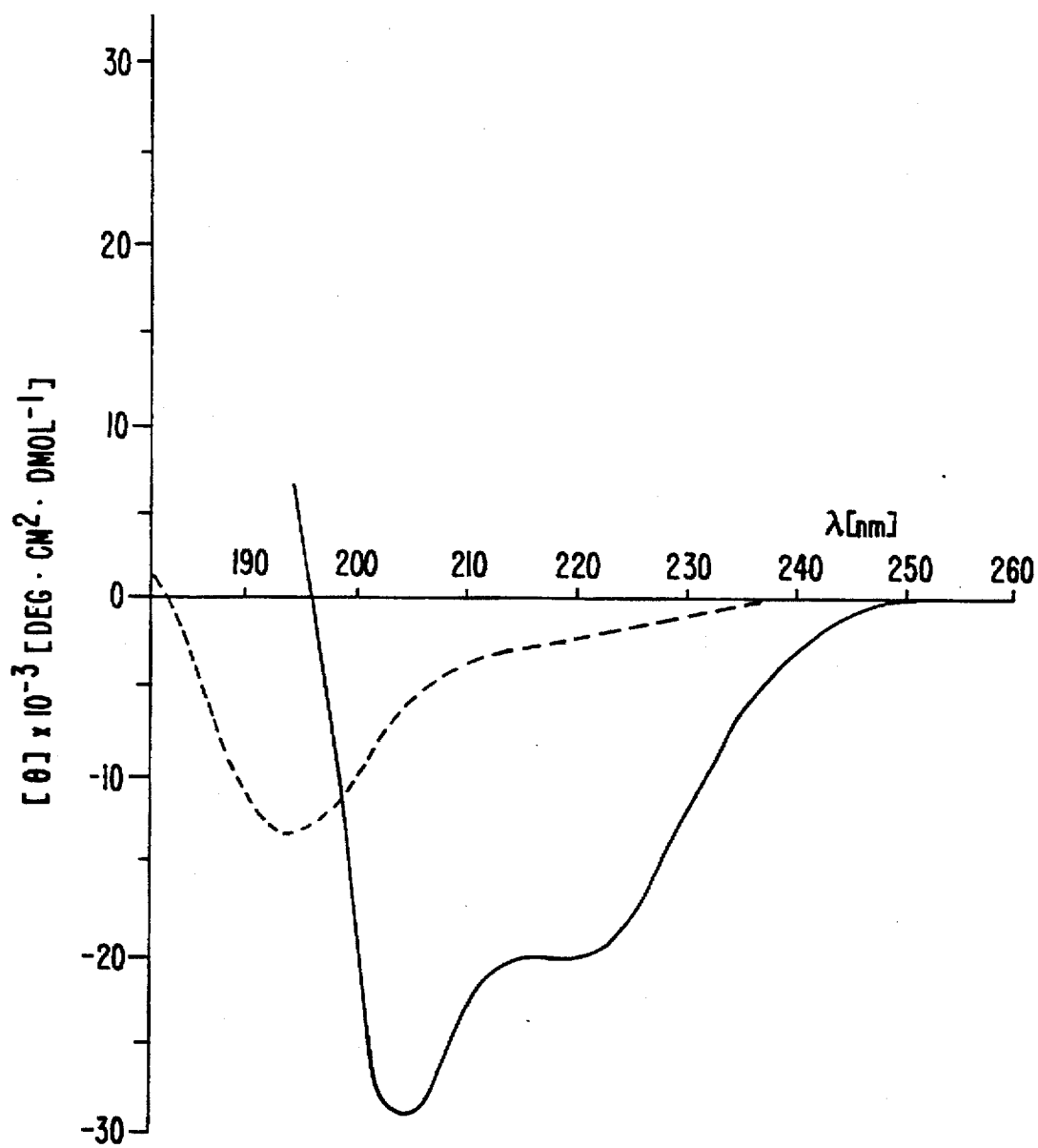
FIG. 10 shows the circular dichroism spectra of both the monomeric peptide (419-436) in the presence (solid line) and absence (broken line) of the nonionic detergent BRIJ®35 (poloyoxyethylene (23) lauryl ether.

Using circular dichroism spectroscopy as described in Example 5, above, the degree of α-helicity of the peptide (419-436) with and without detergent was determined. FIG. 10 shows the circular dichroism spectra of the peptide in phosphate buffered saline (PBS) (broken line) and in PBS with 0.03% Brij 35 (solid line). The shoulder in the solid line at 220 λ indicates the presence of an α-helix in the peptide with detergent. These results were confirmed in assays showing enhanced ability of the peptide monomer to bind CD4 in the presence of detergent.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

---

What is claimed is:

1. A composition comprising a peptomer comprising a plurality of peptide monomers arranged head-to-tail, each peptide monomer comprising a sequence from a CD4 binding region of gp120 from HIV wherein the secondary structure of the peptomer is at least about 20 percent α-helix and wherein antibodies raised against said peptomer are capable of binding to native gp120.

2. The composition of claim 1, wherein each peptide monomer comprises KIKQIINMWQEVGKAMYA (SEQ ID. No. 7).

3. The composition of claim 1, wherein the peptomer is constructed from haloacetyl derivatized peptide monomers.

4